(12) United States Patent
Chen

(10) Patent No.: US 10,288,277 B2
(45) Date of Patent: May 14, 2019

(54) SMART HOME SECURITY DEVICE

(71) Applicant: Kaipo Chen, Taoyuan (TW)

(72) Inventor: Kaipo Chen, Taoyuan (TW)

( * ) Notice: Subject to any disclaimer, the term of this patent is extended or adjusted under 35 U.S.C. 154(b) by 0 days.

(21) Appl. No.: 15/817,276

(22) Filed: Nov. 19, 2017

(65) Prior Publication Data

US 2018/0091715 A1    Mar. 29, 2018

Related U.S. Application Data

(63) Continuation-in-part of application No. 15/391,856, filed on Dec. 28, 2016, and a continuation-in-part of
(Continued)

(30) Foreign Application Priority Data

Dec. 12, 2016    (CN) .......................... 2016 1 1142151

(51) Int. Cl.
| | | |
|---|---|---|
| A61B 5/00 | (2006.01) |
| H04N 7/18 | (2006.01) |
| F21V 33/00 | (2006.01) |
| G08B 21/04 | (2006.01) |
| H04N 5/225 | (2006.01) |
| H04N 5/232 | (2006.01) |
| A61B 5/0205 | (2006.01) |
| G08B 7/06 | (2006.01) |
| G08B 17/00 | (2006.01) |

(Continued)

(52) U.S. Cl.
CPC .......... *F21V 33/0076* (2013.01); *A61B 5/002* (2013.01); *A61B 5/0205* (2013.01); *F21V 33/0064* (2013.01); *F21V 33/0068* (2013.01); *G08B 21/0492* (2013.01); *H04N 5/2253* (2013.01); *H04N 5/2256* (2013.01); *H04N 5/2257* (2013.01); *H04N 5/23216* (2013.01); *H04N 5/23219* (2013.01); *H04N 5/23238* (2013.01); *H04N 7/183* (2013.01); *A61B 5/0022* (2013.01); *A61B 2505/07* (2013.01); *F21V 33/0052* (2013.01); *F21Y 2115/10* (2016.08); *G08B 7/06* (2013.01); *G08B 17/00* (2013.01); *G08B 21/043* (2013.01); *G08B 21/14* (2013.01); *Y04S 20/227* (2013.01); *Y04S 20/228* (2013.01)

(58) Field of Classification Search
None
See application file for complete search history.

(56) References Cited

U.S. PATENT DOCUMENTS

| | | | | |
|---|---|---|---|---|
| 7,467,881 B2 * | 12/2008 | McMillen | ............... | F21S 8/026 362/147 |
| 2013/0029580 A1 * | 1/2013 | Furrer | ............... | G05B 19/0428 454/239 |
| 2014/0001977 A1 * | 1/2014 | Zacharchuk | ........ | H04L 12/2816 315/291 |

* cited by examiner

*Primary Examiner* — David N Werner
(74) *Attorney, Agent, or Firm* — Leong C. Lei

(57) ABSTRACT

A smart home security device includes a security device, which is provided, in the interior thereof, with multiple modules connected with a main control board. The main control board allows an insertion trough provided in the security device to be used in combination with a corresponding expansion module in order to acquire detection signals concerning a body temperature of a target body and temperature and humidity in a manner of interference-reduced manner with accuracy and signal transmission speed increased. An infrared control module provided in the security device is operable to drive a related electrical appliance to have a family member well taken care of for smart home caring.

8 Claims, 14 Drawing Sheets

Related U.S. Application Data application No. 15/219,285, filed on Jul. 26, 2016, now Pat. No. 9,874,334, and a continuation-in-part of application No. 15/133,236, filed on Apr. 20, 2016, now Pat. No. 9,854,641.

(51) Int. Cl.
*G08B 21/14* (2006.01)
*F21Y 115/10* (2016.01)

US 10,288,277 B2

SMART HOME SECURITY DEVICE

CROSS-REFERENCE TO RELATED APPLICATION

This is a continuation-in-part of co-pending U.S. patent application Ser. Nos. 15/133,236, 15/219,285, and 15/391,856 respectively filed on Apr. 20, 2016, Jul. 26, 2016, and Dec. 28, 2016, all being continuation-in-part applications of U.S. patent application Ser. No. 14/258,029 filed on Apr. 22, 2014 (which is a continuation-in-part application of U.S. patent application Ser. No. 13/220,720 filed on Aug. 30, 2011 and now U.S. Pat. No. 9,228,7310), which claim foreign priority of Chinese Patent Application No. 201410089724.9 filed on Mar. 12, 2014 and is now U.S. Pat. No. 9,571,712, and claiming foreign priority of Chinese Patent Application Nos. 201410089724.8, 201510943772.3, 201610146308.6, 201611142151.6, respectively filed on Mar. 12, 2014, Dec. 18, 2015, Mar. 15, 2016 and Dec. 12, 2016; U.S. patent application Ser. No. 15/391,856 being also a continuation-in-part application of U.S. patent application Ser. No. 15/011,646 filed on Jan. 31, 2016, which is now U.S. Pat. No. 9,574,763 and is also a continuation-in part of U.S. patent application Ser. No. 14/258,029, all U.S. Patent Applications and U.S. Patents mentioned above being own by the present Applicant.

TECHNICAL FIELD OF THE INVENTION

The present invention relates generally to a smart home security device, which comprises a main control board arranged in the interior of the device and connected to a detection module that detects a surrounding environment, an image-capturing module that captures an image, an assistance module that provides a reminder, and an expansion module that provides easy connection so that upon inspection and detection of a housing environment, automatic connection is made to peripheral household electrical appliances for controlling the operations thereof to perfect surveillance and security of the living environment.

DESCRIPTION OF THE PRIOR ART

Nowadays, the light-emitting diode (LED) technology is getting mature in various applications, and in addition to the development of techniques regarding energy saving and lighting, manufacturers also focus on the development of styles and functions of LED related devices available in the market to provide multiple functions associated therewith. One of the hottest applications is concerned about products that combine the Wi-Fi technology that has been quite mature for target monitoring through remote operations. Most of the families have elder family members or young children. Most of the adults have to leave home for working and it is generally not possible for them to watch and take care of these family members from time to time. Although attendants for the elders and/or young children may be available, the cost may not be affordable to all the families.

Products of the kind discussed above generally have individual specifications according to model and functionality thereof. In order to add or remove certain features for products to be sold in different areas, manufacturers often need to re-design the entire product. In addition, the compound products having multiple functions involve relatively complicated designs in respect of operations and firmware maintenance thereof and this often causes troubles to users in general uses of these products. In view of the above problem, the present invention is made to help alleviate or overcome such problems.

SUMMARY OF THE INVENTION

The present inventor has been working in the field of research and manufacture of camera based surveillance techniques and have obtained a number of US patents in the field, including U.S. Pat. Nos. 9,228,731; 9,571,712; 9,429,517; 9,460,595; 9,472,070; 9,560,712; 9,574,763; and 9,709,255 and have been continuously devoted in the development of products in response to user's experiences and feedbacks of products of this kind with additional US Patent Applications filed subsequently, including U.S. patent application Ser. Nos. 15/391,856; 15/219,285; and 15/133,236 for making the techniques so developed more popular and more widely used.

Prior art documents in this field is known. For example, US Patent Publication No. 2008/0177646 A1 discloses a work site remote monitoring and employee time tracking system, wherein image of surveillance, together with on-site biometric scanning data, is transferred through a network to a management end in order to determine the movement and behavior of the employees for the purpose of management. Such a system needs an additional device used in combination therewith and involves human labor in the use thereof. Further, Japanese Patent Applicant No. 2012-22579 discloses an LED lighting device in which a standing wave radar is included for detecting the distance and biological or physiological conditions of a human body for driving a light source and an alarm, and is applicable to buildings, transportation vehicles, and even roads. However, a major drawback is that efficient and accurate detection of abnormality of a human body is generally not available and the range of detection is generally short, so that the applicability thereof to a household or interfering environment may not be practical.

Products that are provided with application of modern technology have been developed, for at least some of them, toward artificial intelligence (AI) involved applications, such as Amazon Echo and Google Home that are currently available in the market and are both products concerning smart housekeeping. However, these products provide functionality that generally concerns integration and search of information, for building a device-interconnected application environment through connection and instruction transmission with other devices and equipment.

It is possible to build a household surveillance and protection environment with such smart housekeeping devices. Firstly, novel household electrical appliances that involve built-in WIFI connection and Bluetooth operation must be provided in the household environment and additional sensors, as well as a large amount of wires, are necessarily built, not to mention additional operation of installation, connection, and definition of the sensors and settings of surveillance software, as well as issues concerning compatibility. This is a project require a large amount of labor and time and is certainly not easy for general consumers.

Thus, the present invention provides a smart home security device, which uses a main control board to connect multiple modules for integration of driving operation and the security device is provided with an insertion trough to allow for an expansion module that is provided for external connection to connect to the main control board, so as to allow a user to make a desired combination in an easy way for easy installation in a site where household lighting is necessary and the expansion function and subsequent maintenance can be made easily.

The present invention provides a smart home security device, which comprises: a security device, in which a main control board is provided and the main control board is connected to an image-capture module, an assisting module, a power supply module, a LED module, and at least one or more than one insertion trough and expansion module arranged inside the security device, wherein each module is connectable with the main control board for being driven to operate so that the security device of the present invention may conduct detection of a target body and the surrounding environment to then control the operation of an electrical appliance corresponding thereto.

The present invention uses the main control board to connect and control the modules thereby making it easy for installation in a necessary site in a household environment, wherein through the arrangement of the expansion module for easy insertion to establish connection with the security device, function of expansion and subsequent maintenance are made easy.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
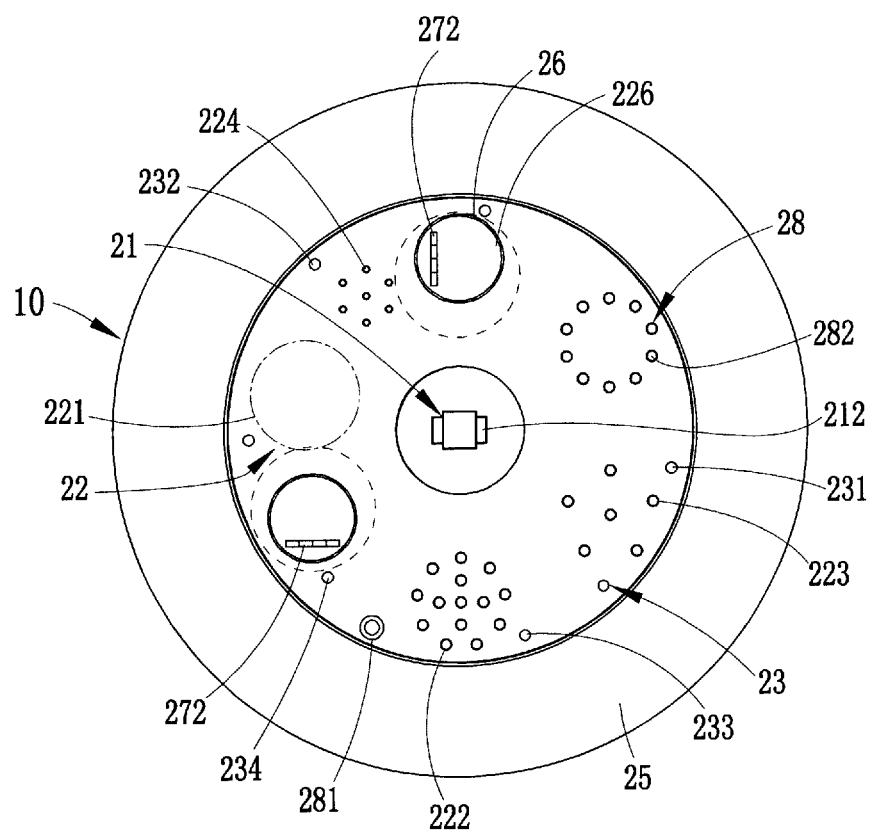
FIG. 1 is a schematic view of the present invention.
Figure 1A:
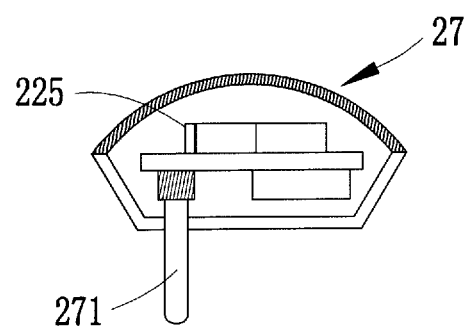
FIGS. 1A and 1B are schematic views showing details of parts of FIG. 1 as indicated by phantom lines linking thereto.
Figure 1B:
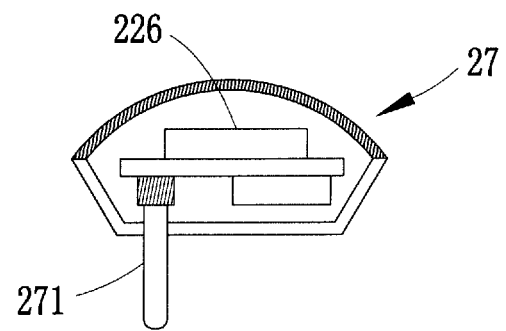
Figure 2:
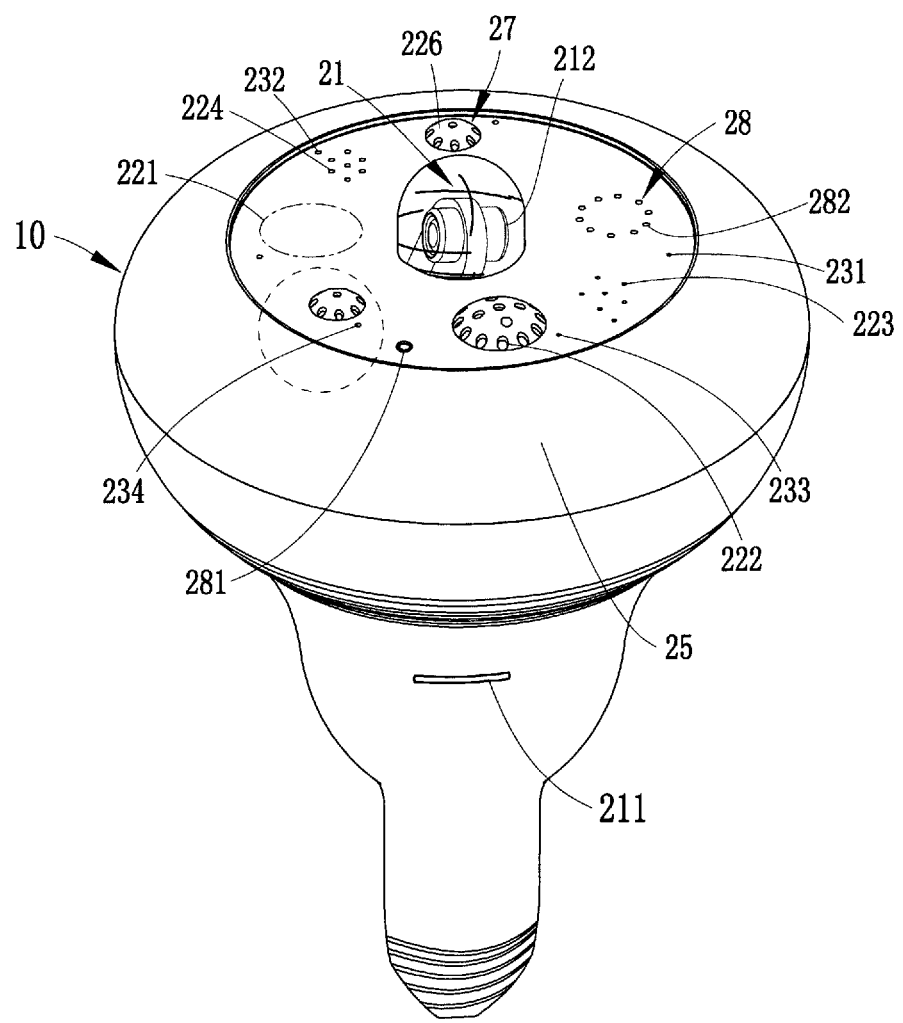
FIG. 2 is a perspective view of the present invention.
Figure 2A:
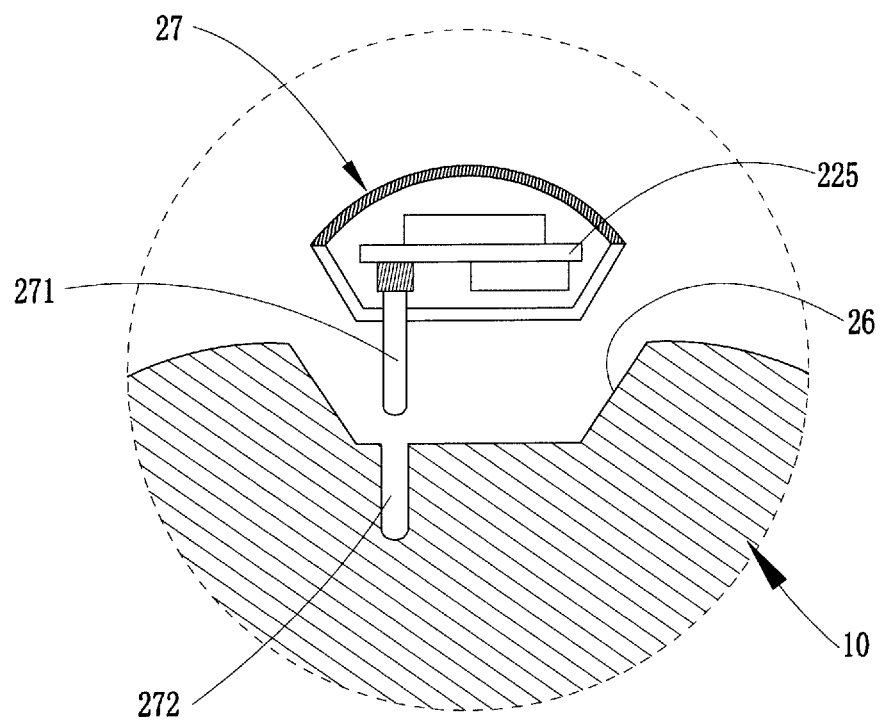
FIG. 2A is a cross-sectional view showing a circled part of FIG. 2.
Figure 3:
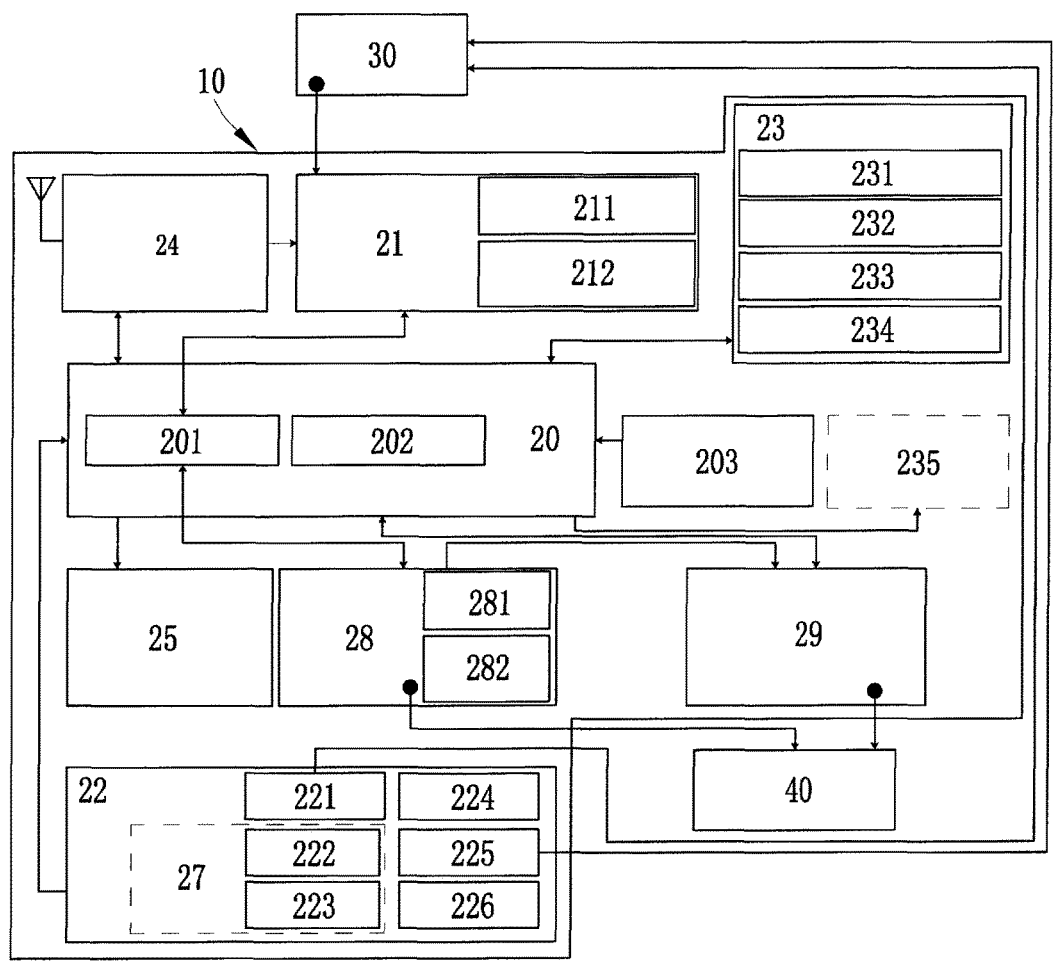
FIG. 3 is a block diagram of the present invention.
Figure 4:
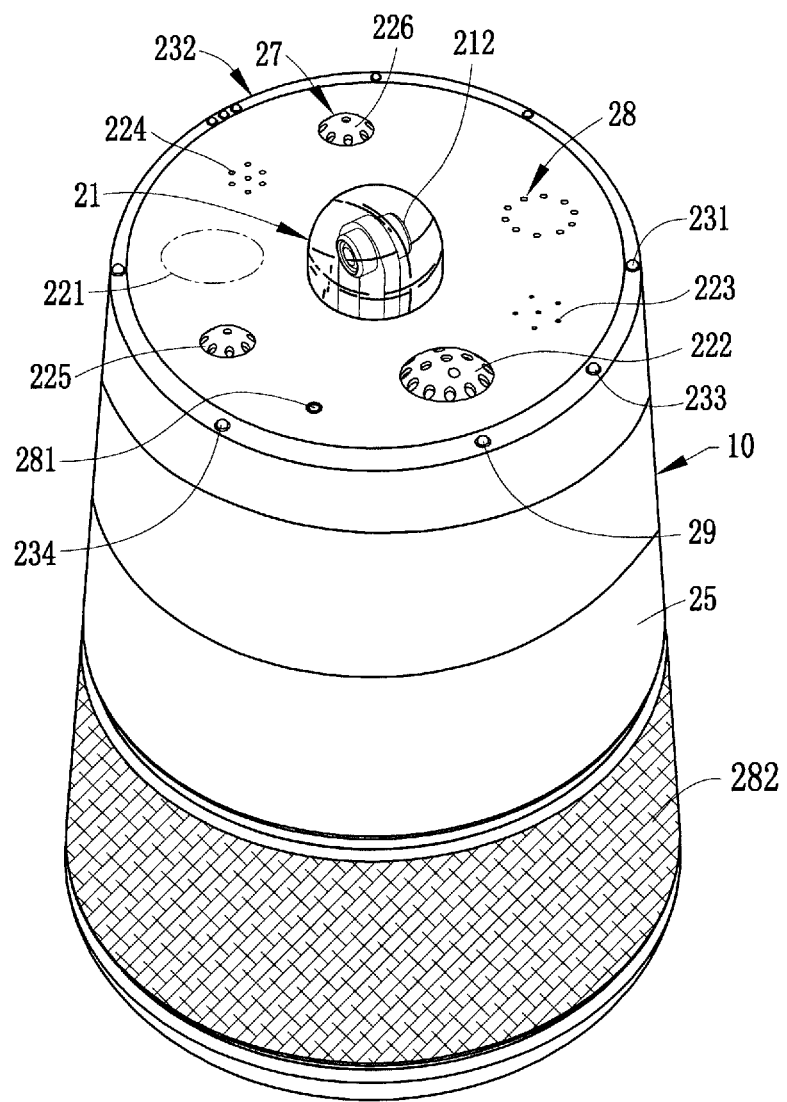
FIG. 4 is a schematic view showing a second embodiment of the present invention.
Figure 5:
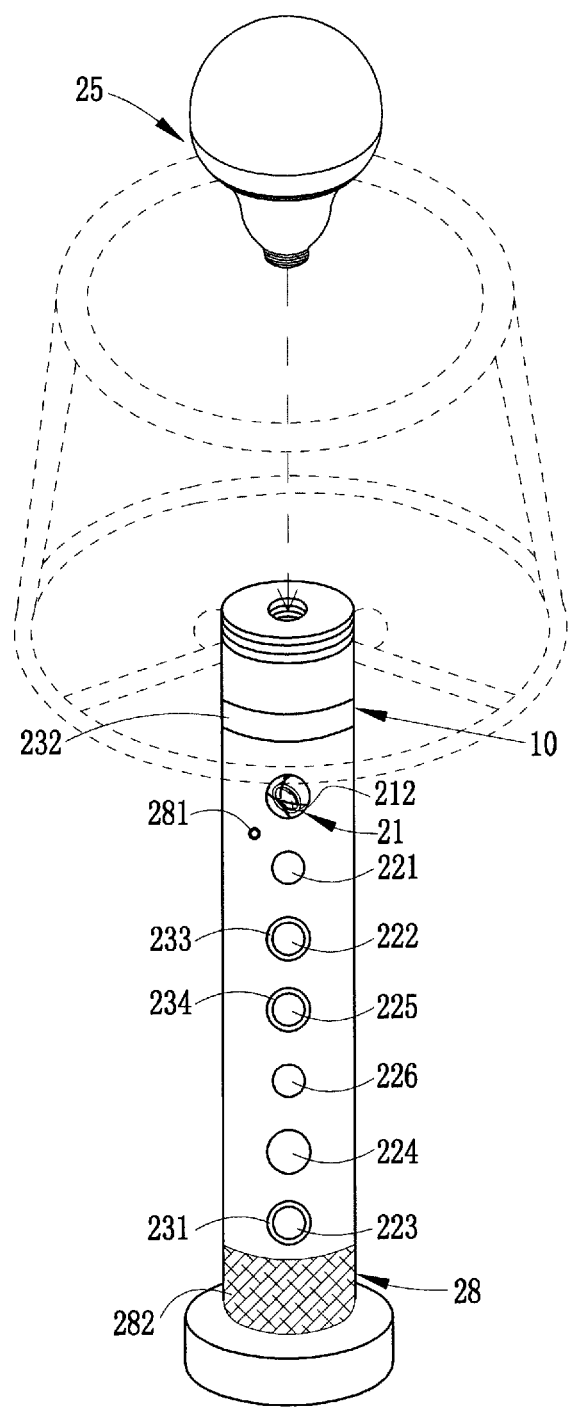
FIG. 5 is a schematic view showing a third embodiment of the present invention.
Figure 6:
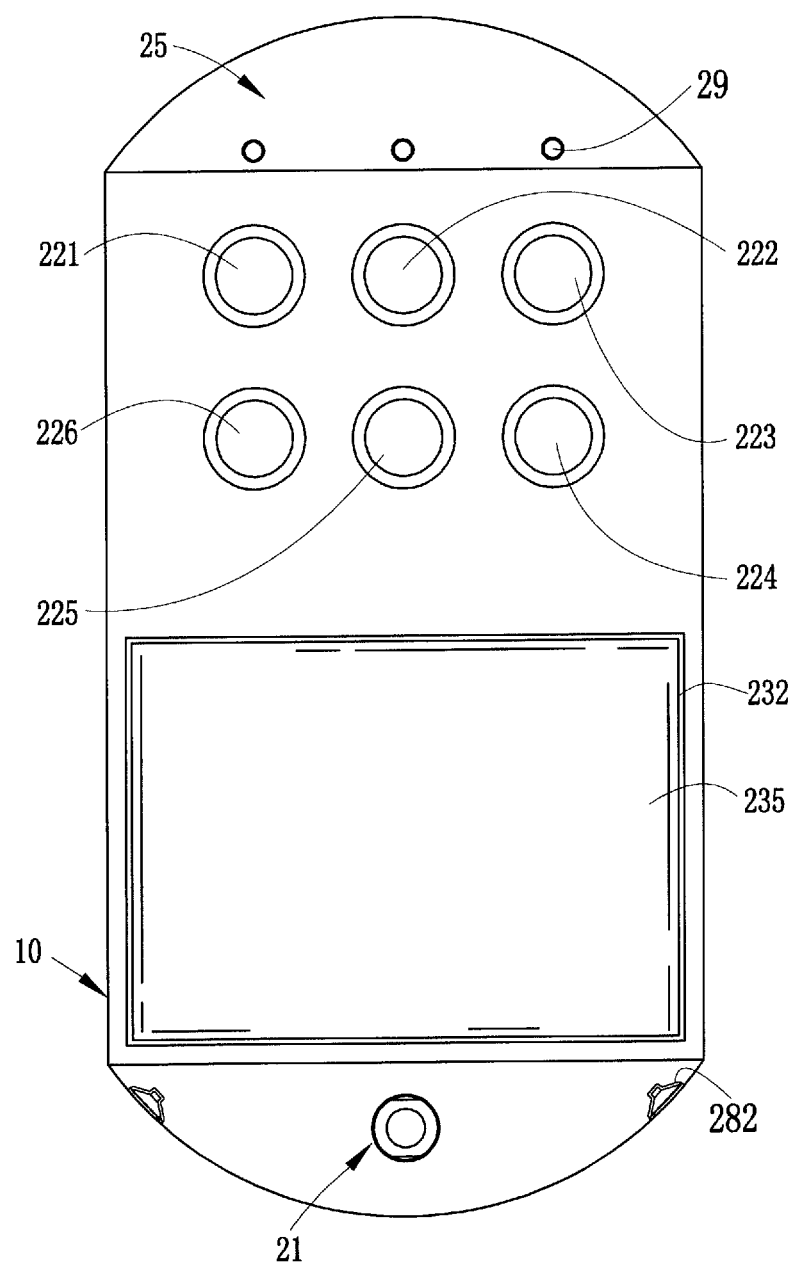
FIG. 6 is a schematic view showing a fourth embodiment of the present invention.
Figure 7:
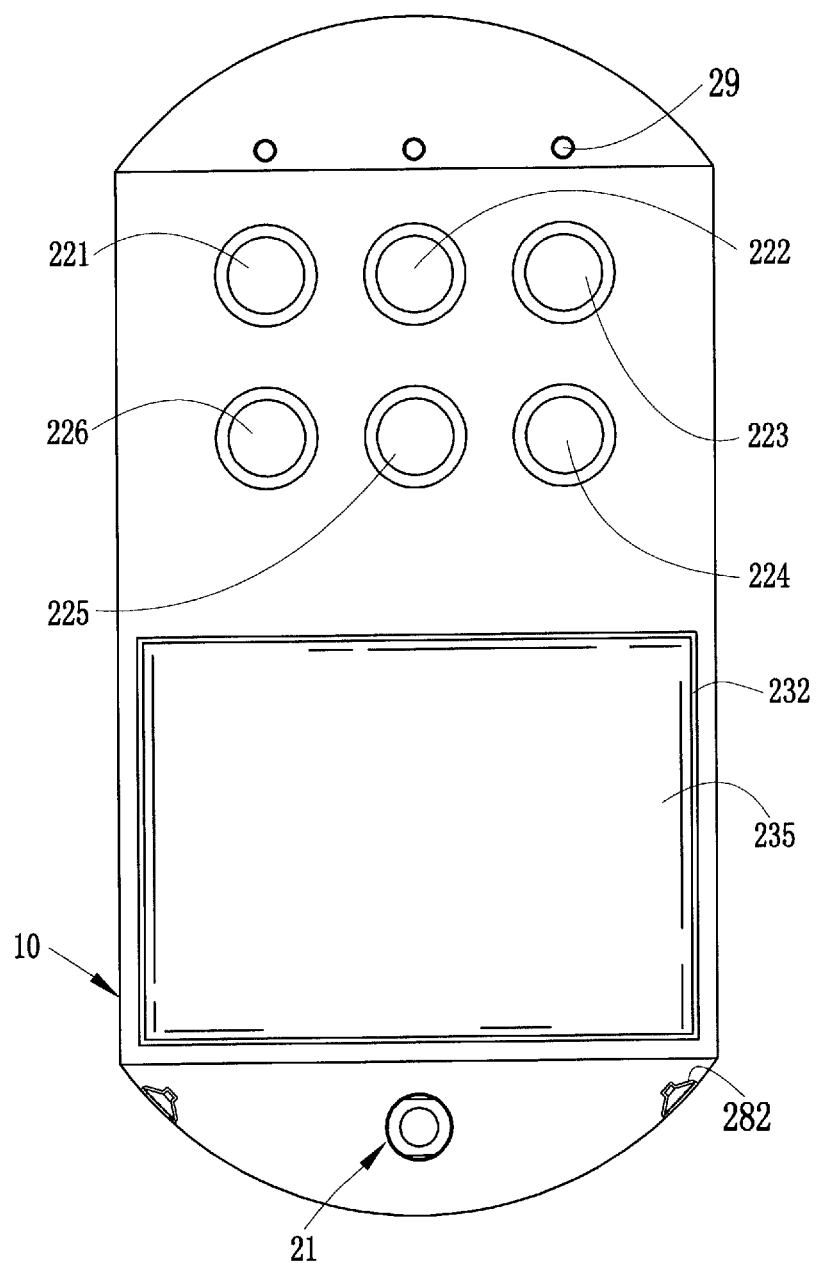
FIG. 7 is a schematic view showing a fifth embodiment of the present invention.

Referring to FIGS. 1-3, a security device (10) is shown, which comprises a main control board (20) arranged in an interior thereof. The main control board (20) is further provided, in the interior thereof, with artificial intelligence (201) and a central processor (202). The artificial intelligence (201) processes and identifies detection signals supplied from detector units and information related to image recognition, facial recognition, and audio recognition and information related to computation, analysis, and conversion, and is operated in combination with the main control board (20) to transmit instructions to an assisting module (23), a wireless communication module (24), and an infrared control module (29) for operations thereof. The main control board (20) is further connected to a power supply module (203).

The main control board (20) is connected to an image-capture module (21), a detection module (22), an assisting module (23), a power supply module (203), a light-emitting diode (LED) module (25), and at least one or more than one insertion trough (26) and expansion module (27) for insertion and/or removal of expansion function, which are arranged and included in the interior of the security device (10).

The image-capture module (21) receives a signal from the main control board (20) and possesses a function of facial recognition to carry out a surveillance operation. The image-capture module (21) comprises multiple lenses (212) to make a full view of 360 degrees in order to provide a dead-zone-free surveillance range, or may alternatively comprise one single lens (212), which may achieve what is desired through a built-in structure for rotation or may alternatively be embodied as a wide-angle lens, but is not limited to the above-described ways of embodiment. The image-capture module (21) may be further connected to a memory card slot (211), and the memory card slot (211) is arranged on a location at an outer side of the security device (10) for easy access by a user for insertion and removal purposes.

The detection module (22) receives a signal from the main control board (20) to have the security device (10) carry out detection of conditions of the surrounding environment and transmits a detection signal to the main control board (20). The detection module (22) may comprises a function of detecting human body functionality and may also comprises elements for other types of detection of the surrounding environment and allows for addition and removal of the functions thereof for adjustment as desired.

The assisting module (23) receives a signal from the main control board (20) to activate a function of assistance. The assisting module (23) is made up of multiple indicators, alarm lights, and a speaker and a microphone, which are respectively operable with the detector units and the main control board (20) so as to provide reminders or alarms through sound and flashing light when the environment changes or problems of body functions of family members.

The power supply module (203) receives a signal from the main control board (20) and the power supply module (203) is connectable with an external power supply and is also connected to a chargeable battery for use in a condition of insufficiency of power of the main control board (20).

The LED module (25) receives a signal from the main control board (20) to allow the security device (10) to carry out a lighting operation. The LED module (25) can be of single warm light, single cold light, or collective side-by-side arrangement of warm light and cold light, or a mixture unit of red, green, and blue light. The main function of the LED is lighting and no limit is imposed to the arrangement thereof.

The insertion trough (26) is provided with a pin insertion hole (272), and the expansion module (27) comprises a pin terminal (271), such that the insertion trough (26) is connectable with the expansion module (27) to allow the main control board (20) to transmit a signal through the insertion trough (26) to activate the operation of the expansion module (27). In a preferred embodiment of the present invention, a body temperature detector unit (225) and a temperature/humidity detector unit (226) are respectively installed in independent expansion modules (27) for use. This is because the operation of the LED module (25) arranged in the security device (10) may cause transfer of heat through a shell thereof and air flow and such heat would affect detector units that are sensitive. This arrangement helps block interference caused by the heat source to thereby reduce errors of detection data and maintain the best result of accuracy and functionality. The expansion module (27) may be modified, through substitution of components thereof/therein to change to a smoke detector unit (222) and/or a gas detector unit (223), and/or a biological recognition unit (221), which may be used in combination with different types of light fixtures or light configurations, or alternatively, the LED module (25) may be installed by means of the expansion module (27) to provide the security device (10) of the present invention with flexibility of including or not including a function of lighting to suit the best need of the surrounding environment as desired by a user.

The detection module (22) comprises: a biological recognition unit (221) that detects parameters of a target body (30) including position, heartbeat, and heart rate. The target body (30) can be a user of various ages in the surrounding environment, such as a child or an elder person, or even a pet. The module is embodied as a Doppler radar that acquires data through frequency of amplitude. The biological recognition unit (221) is generally not affected by the material that makes the security device (10) and can be hidden in the interior so that outside appearance can maintain good looking.

More specifically, the target body (30) relies on the biological recognition unit (221) to conduct an operation that is based on a moving signal of a high frequency band of a breath signal so that when a breath signal is identified and, based on a moving signal, it is identified according to a resident moving within a fixed period of time that the resident is in an abnormal condition. Thus, based on standing wave analysis, detection range can be expanded and high accuracy of detecting abnormality can be achieved. Information obtained with such detection can be transmitted back to the main control panel (3) to be recorded so that in case of abnormality, images and information so detected can be transmitted to a hospital to obtain remote emergent medical treatment instructions to thereby provide a certain degree of effectiveness for surveillance of the elder and young home members. During the process, temperature information of the target body (30) transmitted from the body temperature detector unit (225) to the main control board (20) may be integrated to provide assistance for determining the physiological condition.

Also provided are a smoke detector unit (222) for detecting/inspecting smoke outside the security device (10), a gas detector unit (223) for detecting/inspecting harmful gases outside the security device (10), an air detector unit (224) for detecting/inspecting the content of suspension particles in an environment outside the security device (10), a body temperature detector unit (225) for detecting/inspecting a body temperature of a family member staying in the environment outside the security device (10), and a temperature/humidity detector unit (226) for detecting/inspecting a temperature and/or humidity in the environment outside the security device (10). All these units are connected to the main control board (20), so that the main control board (20) may control transmission of signal associated with each of the units to drive and active a corresponding function.

The temperature/humidity detector unit (226) may detect data of temperature and moisture content in the present environment and the detected data are fed back to the artificial intelligence (201) of the main control board (20) for processing and a message in response thereto is transmitted by the main control board (20) to a wireless device.

The assisting module (23) comprises: a gas alarm indicator (231), an air quality indicator (232), a smoke alarm indicator (233), and a body temperature reminder indicator (234).

The gas alarm indicator (231) is connected to and operable in combination with the gas detector unit (223) to detect/inspect if harmful gases (such as nitrogen monoxide, methane, propane, isobutene, natural fossil fuel vapors) are present in a detection range and is normally ON as a normal operation condition. In case of power outage and shortage of power supply, flashing light is emitting and is of priority of activation in order to prevent severe catastrophes of fire and gas explosion to ensure security of household environment. During the process, the main control board (20) may be set in operation to drive a speaker (282) of an audio module (28) and the gas alarm indicator (231) to issue alarms.

The air quality indicator (232) is operable in combination with the air detector unit (224) to detect/inspect particulate matter (PM) or suspension particles in air and to transmit related data, through connection of the main control board (20) with the wireless communication module (24), to a wireless device preset by a user, while the air quality indicator (232) is operable to emit, in a persistent way for a long period of time, light of different colors to indicate the air quality, wherein blue indicates a normal condition, yellow indicate an intermediate condition, and red indicates the worst condition. The displayed color of light can be changed according to practical production requirement and is not to the colors discussed.

The smoke alarm indicator (233) is operable in combination with and connected to the smoke detector unit (222) to emit a flashing reminder according to a condition of detection, or to drive, through the main control board (20), the speaker (282) of the audio module (28) to issue alarm. The smoke alarm indicator (233) is of a normal ON condition as a normal operation thereof.

The body temperature reminder indicator (234) is operable in combination with and in connection with the body temperature detector unit (225) for measurement of body temperature of a family member such that a reminder or alarm is issued when the measured data is greater than a normal temperature and to transmit notification to a handheld devices of family members when the measured body temperature of the family member is higher than a normal temperature and/or exceeds a preset threshold. After a lapse of predetermined period of time, if the body temperature of the family member is still higher than the normal temperature, then a more significant reminder through indication light is provided so that the physical condition of the family member can be effectively monitored. The body temperature detector unit (225) is also operable to activate the image-capture module (21) to can out videotaping or image capturing.

The detection module (22), the assisting module (23), and the image-capture module (21) arranged in the security device (10) can be selected to install with just one single module or multiple modules are installed. In addition the detector units included in the detection module (22) can be increased or decreased for the number thereof involved according to practical requirement of production and the number actually involved is not specifically constrained.

The main control board (20) is structured to include the artificial intelligence (201) and a plurality of chips for ancillary purpose and storage of data in order to process the full-view image acquired with the image-capture module (21) so as to determine the conditions of the environment and a predetermined family member and to provide settings and connection for corresponding handling operations and to drive the corresponding functions to proceed. For example, the operation may be to determine if the condition of the environment is normal and the current situation of the family member. If the recording data of the family member of the environment show a significant variation, then image capturing, facial recognition, and videotaping are carried out and, even more, corresponding audio alarm or alarm light may be activated and communication with other family members may be made or sending rescue request to emergency handling agency or facility.

The security device (10) is further provided therein with a wireless communication module (24), an audio module (28), and an infrared control module (29). The wireless communication module (24) is operable with WIFI, LIFI, Bluetooth, Z-WAVE, ZigBee, or other wireless communication techniques for transmission to external devices, such as a tablet computer, a smart phone, a vehicle connection network, a handheld device, or a wearable device. The audio module (28) is provided with a microphone (281) and a speaker (282) for the purposes of audio recognition and input and output of sounds so that oral instruction given by a target body (30) can be made to the main control board (20) to have the security device (10) establish connection with electrical appliance to conduct a corresponding operation. The infrared control module (29) provides transmission and receiving through infrared signals, audio or wireless control for connection with the detection module (22) to automatically control household electrical appliances, such as air-conditioner, air purifier, dehumidifier, television, and light, so that light can be automatically turned on when a user enters a living room and other electrical appliances so connected may be activated according to settings made by the user. When the user leaves, the light and the electrical appliances so connected are automatically shut down. The activation of the electrical appliance is primarily based on ad controlled by the main control board (20) for activation; however after the electrical appliance (40) is activated, if the target body (30) gives oral instruction to the audio module (28) to control the electrical appliance (40), then the oral instruction may take priority over the main control board (20) to ease the operation of being controlled by the user.

In a second embodiment of the present invention, a security device (10) that is positionable on a desk or a table is provided, which may comprises components similar to those described in the previous embodiment, but with the speaker (282) of the audio module (28) being moved to arranged at a lower portion of the security device (10) and the LED module (25) being arranged a location above the speaker. The gas alarm indicator (231), the air quality reminder indicator (232), the smoke alarm indicator (233), and the body temperature reminder indicator (234) of the assisting module (23) are set at a circumferential area of a top of the security device (10) such that an annular light is formed along the circumference, or multiple individual lights may be provided for displaying and indication, in order to allow the user to recognize if the current environment and the target body (30) have abnormal conditions, and is not limited to the style of arranging lighting along the circumference. The security device (10), as compared to the primary embodiment provided previously, is modified just for the outside appearance and thus no repeated description is necessary. The LED module (25) may be omitted so that the security device (10) of the second embodiment allows a user to selectively between two types one with lighting and the other without lighting.

In a third embodiment of the present invention, a desk lamp is provided, which comprises components that are similar to the those of the previous embodiments, but the image-capture module (21), the detection module (22), and the assisting module (23) are moved to a circumference of the security device (10), wherein on the outer side of the part where each detection and recognition unit of the detection module (22) are arranged, indicators and alarm lights associated therewith are provided to allow institutive observation and identification of the information provided thereby, wherein only the air quality indicator (232) is operable for independent displaying for the functionality is used for regular condition, and the LED module (25) is embodied as a regular LED light bulb mounted atop the security device (10). The other operations are generally the same so that no repeated description is necessary.

In a fourth embodiment of the present invention, a wall-mounted light is provided, which comprises components that are similar to the those of the previous embodiments, but a difference of the security device (10) is that the assisting module (23) is directly mounted and included in a LCD display panel (235) mounted in a lower portion of the security device (10) for displaying. The LCD display panel (235) can be touch-controllable and connected to the main control board (20), of which the corresponding operations are similar to those of the preferred embodiment described above as being driven and controlled through collaborate operations of the main control board (20) and the artificial intelligence (201) and the central processor (202) included therein, but just involved with the LCD display panel (235) to improve operation easiness for the user. The LCD display panel (235) is provided on an outer perimeter with the air quality indicator (232) for displaying the current environment condition. The LCD display panel (235) may be replaced with different types of displays, such as an LED display or an OLED (Organic Light-Emitting Diode), and no specific limitation is imposed. A fifth embodiment of the present invention is similar to the fourth embodiment, but just with the LED module (25) is omitted from the security device (10) to provide an additional model as an option for the user.

Figure 8:
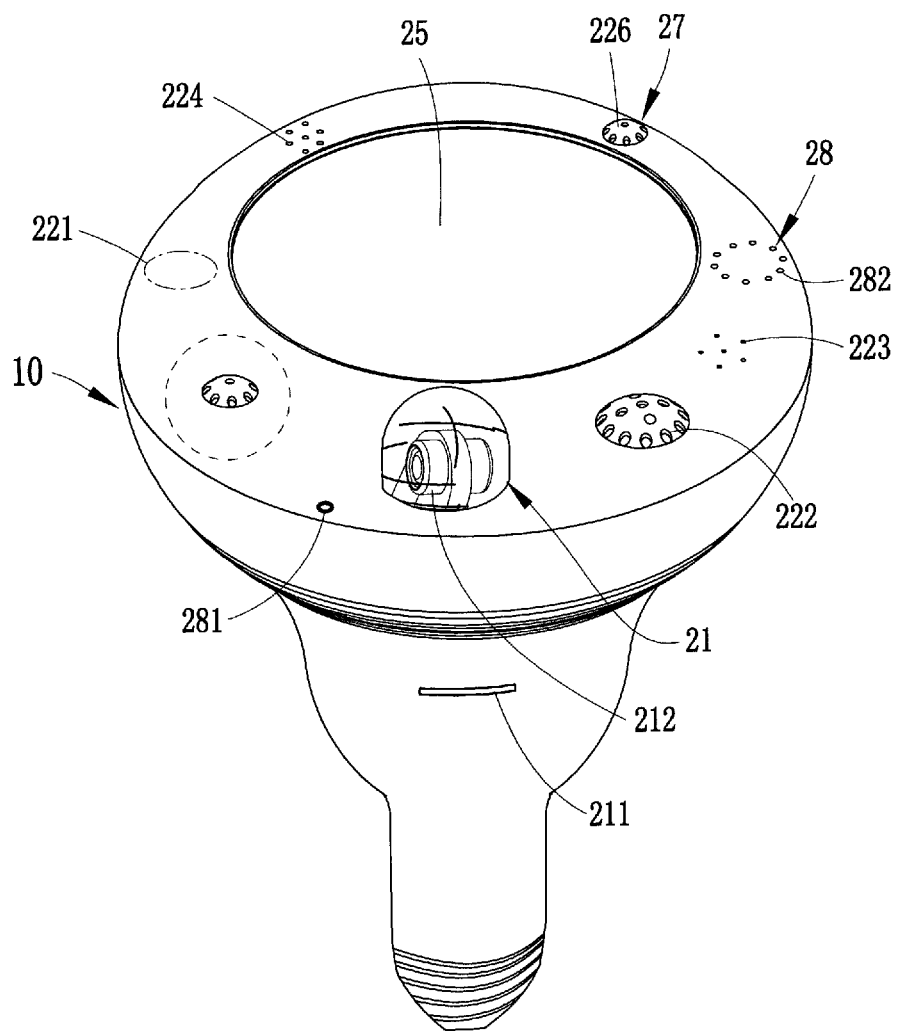
FIG. 8 is a schematic view showing a sixth embodiment of the present invention.
Figure 8A:
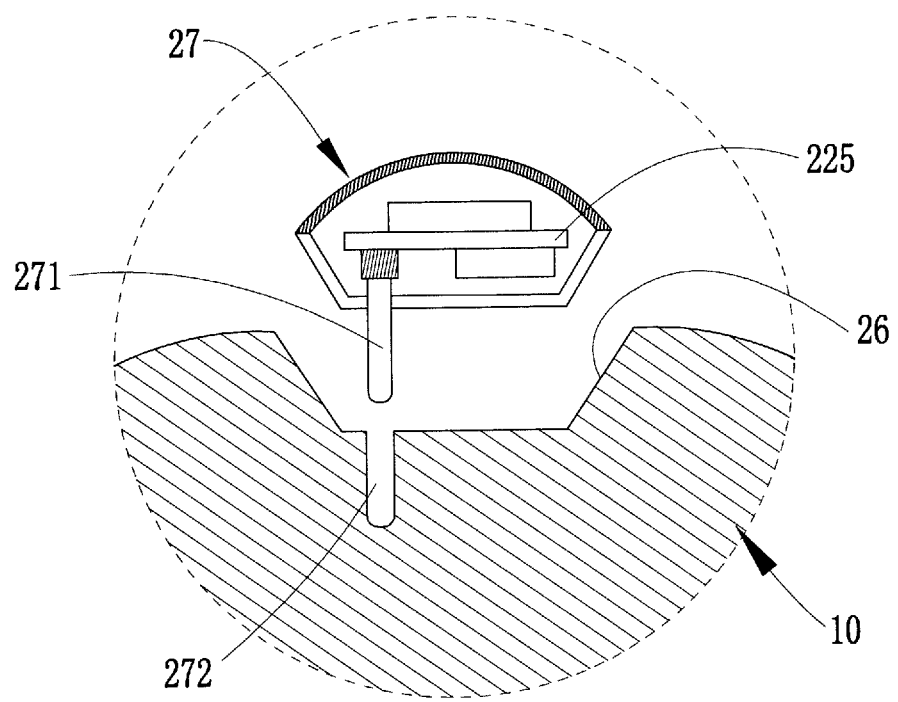
FIG. 8A is a cross-sectional view showing a circled part of FIG. 8.
Figure 9:
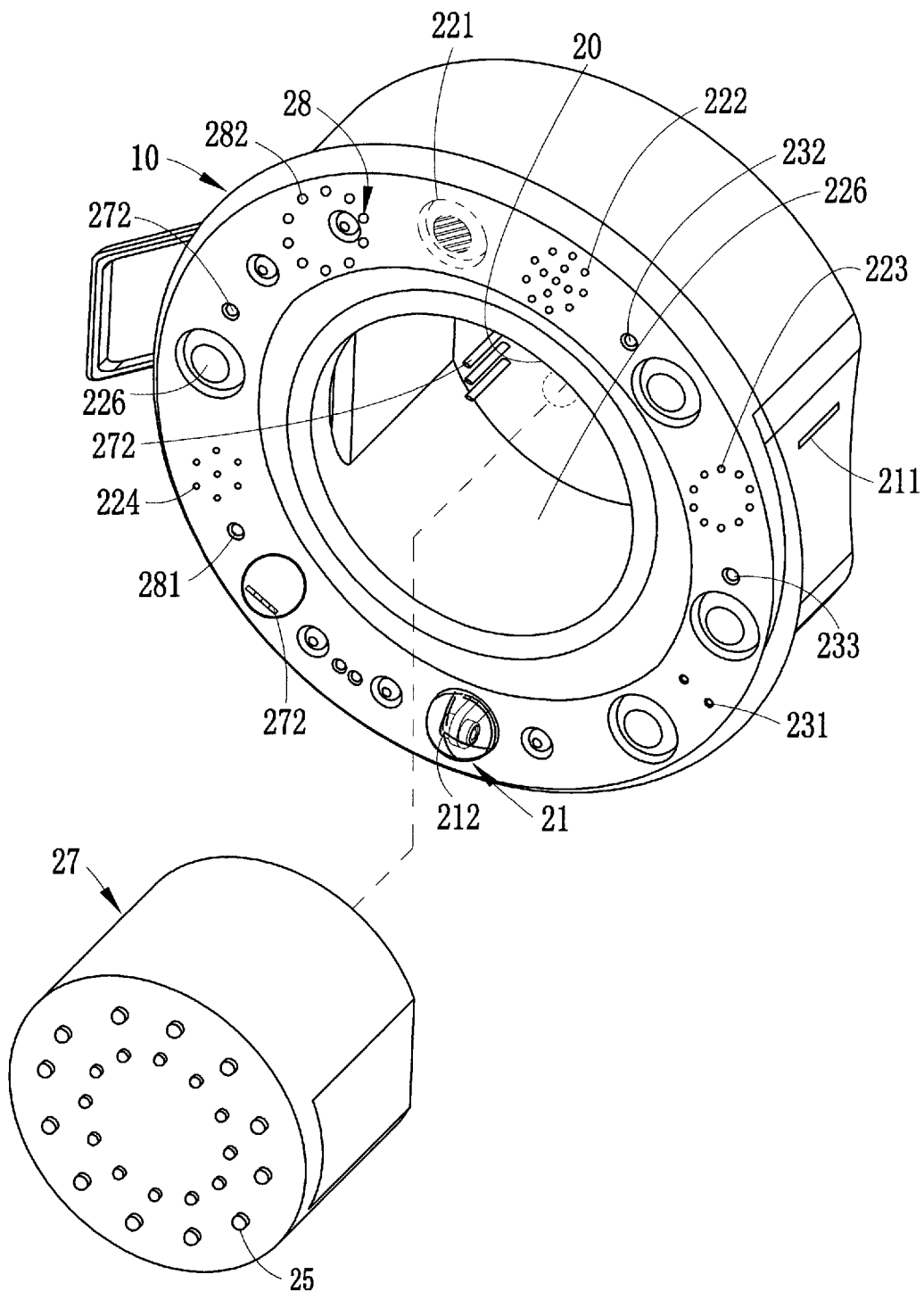
FIG. 9 is a schematic view showing a seventh embodiment of the present invention.
Figure 9A:
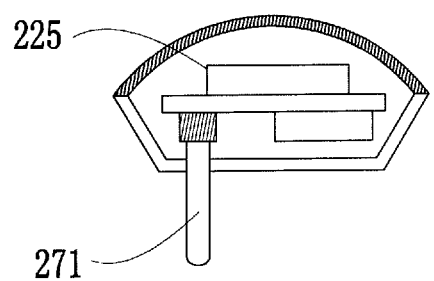
FIG. 9A is a schematic view showing details of a part of FIG. 9 as indicated by a phantom line linking thereto.

In a sixth embodiment, as shown in FIG. 8, components are similar to those of the preferred embodiment of the present invention and a difference is that the locations of the components that are originally arranged in inner and outer portions (or inner and outer layers) are modified such that the inner portion or inner layer includes the LED module (25), while the image-capture module (21), the detection module (22), and the assisting module (23) are moved to the outer portion or the outer layer. The purpose of the modification is to concentrate lighting of the LED module (25) on the center, while the modules of the outer layer may be made more flexibile in the operation, functionality, achievable purposes, and use thereof through the expansion module (27), repeated description being omitted herein. A seventh embodiment of the present invention is shown in FIG. 9 and has a structure similar to the previous embodiment but with the expansion module (27) being arranged, in the form of the LED module (25), at the center of the entire structure so that when there is no need for lighting, direct withdrawal of the expansion module (27) can be made, but with the other operations of surveillance being preserved, whereby the target body (30) may take activity under a secured condition. This is a simple modification of the previously described structure and repeated description will be omitted.

In summary, the present invention provides a smart home security device, wherein through multiple detection modules (22) arranged in the interior thereof, information acquired can be transmitted to the main control board (20) arranged inside the security device (10) so that through corresponding connection of the wireless communication module (24), the infrared control module (29), and the LED module (25), electrical appliances (40) can be connected and thus in respect of the physiological condition of a target body (30) and based on the artificial intelligence (201) and the central processor (202) to have the electrical appliance and the information so acquired improved in respect of the response thereof, predicting habits and preference of the target body (30) to built up associated operation, making the application to smart home more versatile and vivid.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A smart home security device, which is operable to drive multiple the target body and electrical appliances, comprising:
   a security device;
   a main control board arranged inside the security device, the main control board being connected to an image-capture module, a detection module, an assisting module, a power supply module, a light-emitting diode (LED) module, and at least one or more than one insertion trough and expansion module for insertion and removal of expansion function arranged inside the security device;
   the image-capture module receiving a signal from the main control board to carry out a surveillance operation;
   the detection module for making the security device carry out detection of a surrounding environment and transmitting a detection signal to the main control board;
   the assisting module for receiving a signal from the main control board to activate an auxiliary function;
   the LED module for receiving a signal from the main control board to have the security device carry out a lighting operation;
   the insertion trough being operable in combination with one expansion module for connection such that the insertion trough transmits a signal of the main control board to activate an operation of the expansion module;
   wherein the detection module further comprises:
      a biological recognition unit that detects position, heartbeat, and heart rate of a target body;
      a smoke detector unit that detects smoke outside the security device;
      a gas detector unit that detects a harmful gas outside the security device;
      an air detector unit that detects contents of particulate matter in an environment outside the security device;
      a body temperature detector unit that detects a body temperature of the target body in an environment outside the security device; and
      a temperature/humidity detector unit that detects a temperature and a humidity level of an environment outside the security device, these units being connected to the main control board so that the main control board controls a signal transmitted from each of the units to drive a corresponding function.

2. The smart home security device according to claim 1, wherein the assisting module further comprises:
   a gas alarm indicator;
   an air quality indicator;
   a smoke alarm indicator; and
   a body temperature reminder indicator, these indicators being operable in combination with information acquired with the detection module and transmitted to the main control board for identification and determination to emit light for displaying and remaindering.

3. The smart home security device according to claim 1, wherein the expansion module further comprises a body temperature detector unit connected to the main control board to detect a body temperature of a target body in the surrounding environment of the security device and transmitting a detection signal to the main control board.

4. The smart home security device according to claim 1, wherein the expansion module further comprises a temperature/humidity detector unit connected to the main control board to detect temperature and humidity of the surrounding environment outside the security device and transmitting a detection signal to the main control board.

5. The smart home security device according to claim 1, wherein the expansion module allows for an LED module to be alternatively installed in the expansion module for connection with the main control board.

6. The smart home security device according to claim 1, wherein the security device further comprises:
   an LCD display panel having operation of touch control and displaying and being arranged outside the security device and connected to the main control board to receive and transmit a signal from and to the main control board; and
   an air quality indicator arranged along a perimeter of the LCD display panel.

7. The smart home security device according to claim 1, wherein the detection module, the assisting module, and the image-capture module are each arranged with a single one or multiple ones.

8. The smart home security device according to claim 1, wherein the detection module is increased or decreased in number according production requirement.

* * * * *